US011141315B2

(12) United States Patent
Hua et al.

(10) Patent No.: US 11,141,315 B2
(45) Date of Patent: Oct. 12, 2021

(54) NOISE-REDUCING EARMUFF

(71) Applicant: Goertek Technology Co., Ltd., Qingdao (CN)

(72) Inventors: Yang Hua, Qingdao (CN); Ze Wang, Qingdao (CN); Xiaofeng Wen, Qingdao (CN)

(73) Assignee: Goertek Tehnology Co., Ltd., Qingdao (CN)

( * ) Notice: Subject to any disclaimer, the term of this patent is extended or adjusted under 35 U.S.C. 154(b) by 0 days.

(21) Appl. No.: 16/770,265

(22) PCT Filed: Dec. 19, 2017

(86) PCT No.: PCT/CN2017/117215
§ 371 (c)(1),
(2) Date: Jun. 5, 2020

(87) PCT Pub. No.: WO2019/109389
PCT Pub. Date: Jun. 13, 2019

(65) Prior Publication Data
US 2020/0397618 A1 Dec. 24, 2020

(30) Foreign Application Priority Data

Dec. 7, 2017 (CN) .......................... 201711289109.1

(51) Int. Cl.
*A61F 11/14* (2006.01)
*H04R 3/02* (2006.01)
(52) U.S. Cl.
CPC ................ *A61F 11/14* (2013.01); *H04R 3/02* (2013.01); *A61F 2011/145* (2013.01)

(58) Field of Classification Search
CPC .. A61F 11/14; A61F 2011/145; H04R 1/1083; H04R 3/02
USPC ..................................... 381/72, 94, 354, 372
See application file for complete search history.

(56) References Cited

U.S. PATENT DOCUMENTS

| 7,740,104 B1 * | 6/2010 | Parkins .................. A61F 11/08 181/135 |
| 9,668,042 B1 | 5/2017 | Kim et al. |
| 10,034,086 B2 * | 7/2018 | Sapiejewski ............. H04R 3/02 |
| 2018/0242082 A1 * | 8/2018 | Hua ..................... H04R 1/1008 |

FOREIGN PATENT DOCUMENTS

| CN | 201616892 U | 10/2010 |
| CN | 201937804 U | 8/2011 |
| CN | 102421043 A | 4/2012 |
| CN | 104363549 A | 2/2015 |
| CN | 204948303 U | 1/2016 |

* cited by examiner

*Primary Examiner* — Vivian C Chin
*Assistant Examiner* — Friedrich Fahnert
(74) *Attorney, Agent, or Firm* — Baker Botts, L.L.P.

(57) ABSTRACT

The present disclosure discloses a noise-reducing earmuff, comprising: an earmuff shell forming an earmuff cavity; a separator being installed in the earmuff cavity and forming an independent chamber; and a conduit being installed on the separator, the conduit being provided with an opening at each of the two ends thereof; wherein one of the openings being located in the chamber, and the other extending out of the chamber and being located in the earmuff cavity; wherein the chamber and the conduit form a low-frequency resonator whose resonance frequency is equivalent to a corner frequency of a low-pass filter formed by the earmuff.

5 Claims, 5 Drawing Sheets

NOISE-REDUCING EARMUFF

CROSS-REFERENCE TO RELATED APPLICATIONS

This application is a National Stage of International Application No. PCT/CN2017/117215, filed on Dec. 19, 2017, which claims priority to Chinese Patent Application No. 201711289109.1, filed on Dec. 7, 2017, both of which are hereby incorporated by reference in their entireties.

TECHNICAL FIELD

The present disclosure belongs to the technical field of noise protection, and specifically relates to a protective earmuff or earphone product for insulating ambient noise.

BACKGROUND

In the field of high-frequency noise protection, protective earmuffs can achieve a good performance of high-frequency noise insulation. For people working in special environments, wearing protective earmuffs can effectively protect their ears.

At the present stage, a thick earmuff shell is typically used for a traditional protective earmuff to provide a large-sized earmuff cavity, in order to effectively insulate from low-frequency noise. The earmuff shell and the earmuff cavity can form a low-pass filter to substantially insulate from high-frequency ambient noise, so that noise entering the earmuff cavity through the earmuff shell come from essentially a low frequency part of the ambient noise which encompasses frequencies lower than the corner frequency of the low-pass filter. A thicker earmuff shell and a larger earmuff cavity would lead to a lower corner frequency of the low-pass filter, which in turn enables noise on more frequency bands to be filtered out, and improves noise insulation performance of the earmuff. However, this traditional design of the protective earmuffs produces earmuffs that are not only bulky and ugly, but also heavy and uncomfortable to wear, thereby seriously affecting the wearer's using experience. What is more, passively insulated noise entering the earmuff cavity exhibits a noise rise and noise amplification phenomenon at or near the corner frequency; where there is long-term existence of amplified partial frequency band energy in the ambient noise, it would cause fatigue of the wearer and even irreversible hearing damage after long-term use.

SUMMARY

The purpose of the present disclosure is to provide a noise-reducing earmuff, which has a low-frequency resonator added in a cavity of the earmuff to absorb low-frequency noise energy therein, thereby improving noise insulation performance of the earmuff while effectively restraining the volume of the earmuff and reducing the weight thereof.

To solve the above technical problems, the present disclosure uses the following technical solutions:

In one aspect of the present disclosure, a noise-reducing earmuff is provided, which includes an earmuff shell forming an earmuff cavity, a separator, being installed in the earmuff cavity and forming an independent chamber, and a conduit being installed on the separator, the conduit being provided with an opening at each of the two ends thereof, wherein one of the openings being located in the chamber, and the other extending out of the chamber and being located in the earmuff cavity; wherein the chamber and the conduit form a low-frequency resonator whose resonance frequency is equivalent to a corner frequency of a low-pass filter formed by the earmuff.

Further, an opening is formed on one side of the earmuff shell which side faces the human ear, and an ear-covering is installed on the earmuff shell at the opening to improve wearing comfort of the earmuff; for the earmuff installed with an ear-covering, the corner frequency of the low-pass filter may be determined by an equivalent inductance of the earmuff shell and an equivalent capacitance of the earmuff cavity and ear-covering.

In order to expand volume of the chamber of the low-frequency resonator, the chamber is preferably filled with a sound absorbing material, so as to increase the equivalent capacitance value of the chamber and further reduce the resonance frequency.

In the case where the earmuff is an earmuff in a headphone, a rear cavity of the speaker in the earmuff can be simply taken as the chamber, and a separator is provided in the rear cavity of the speaker. When the speaker outputs sound, the separator blocks the opening of the conduit located in the chamber to prevent the low-frequency energy in the audio signal or the communication signal from being cancelled; when the speaker outputs no sound, the separator is apart from the opening of the conduit located in the chamber, and the low-frequency noise energy in the earmuff is absorbed by a low-frequency resonator formed by the rear cavity of the speaker and the conduit so as to reduce low-frequency noise.

Preferably, an armature in an electromagnetic relay can be used as the separator to block the opening of the conduit, that is, when the speaker receives an audio signal, the electromagnetic relay generates a magnetic field to displace the armature by attraction and to block the opening of the conduit located in the chamber; when the speaker receives no audio signal, the electromagnetic relay releases the armature to keep the armature apart from the opening of the conduit located in the chamber.

In order to control the electromagnetic relay to act accurately, in the present disclosure, the noise-protecting earmuff is also provided with a comparator. The comparator has two input terminals configured to respectively receive a trigger voltage and the audio signal, wherein the output terminal is connected to a control terminal of a switching element, and a switching path of the switching element is connected in a power supply circuit of a coil of the electromagnetic relay; and the amplitude of the trigger voltage is lower than the amplitude of a bias voltage in the audio signal; wherein: when an audio signal is received, a output level of the comparator controls the switching element to conduct, and the power supply circuit of the coil of the electromagnetic relay is connected, so that the coil is energized to generate a magnetic field and displace the armature by attraction and thus blocking the opening of the conduit located in the chamber. At this time, the rear cavity of the speaker and the conduit cannot form a low-frequency resonator and will not absorb the low-frequency energy in the earmuff, thus ensuring normal output of the low-frequency energy in audio signals or communication signals.

In another aspect of the present disclosure, a noise-reducing earmuff is also proposed, including an earmuff shell forming an earmuff cavity, a separator installed in the earmuff cavity and forming an independent chamber, and a passive radiator installed on the separator; wherein the chamber and the passive radiator form a low-frequency resonator whose resonance frequency is equivalent to the corner frequency of the low-pass filter formed by the earmuff.

In yet another aspect of the present disclosure, a noise-reducing earmuff is also proposed, including an earmuff shell forming an earmuff cavity, a separator installed in the earmuff cavity and forming an independent chamber, a passive radiator installed on the separator and a conduit; wherein one of the openings at both ends of the conduit is located in the chamber, and the other extends out of the chamber and is located in the earmuff cavity; wherein the chamber, the passive radiator and the conduit form a low-frequency resonator whose resonance frequency is equivalent to the corner frequency of the low-pass filter formed by the earmuff.

Compared with the prior art, the advantages and positive effects of the present disclosure possesses the following advantages and positive effects: in solving the problem of noise insulation by earmuff, the present disclosure sublates the traditional structural design of thickening the earmuff shell and increasing the earmuff cavity, instead, the present disclosure adopts the approach of providing a low-frequency resonator in the earmuff cavity, which utilizes resonance sound absorption effect of the low-frequency resonator to absorb the noise energy of the passively insulated sound in the earmuff cavity near the resonance frequency of the low-frequency resonator, thereby avoiding the problem of noise rise and noise amplification of the passively insulated sound in the low frequency part and achieving a balance of noise attenuation energy and attenuation frequency band in the earmuff cavity, which is not only beneficial to protecting the wearer's hearing, but also reduces the overall size of the earmuff and improves the wearer's comfort.

BRIEF DESCRIPTION OF THE DRAWINGS

After reading the detailed description of the embodiments of the present disclosure in combination with the accompanying drawings, other features and advantages of the present disclosure will become more apparent.

DETAILED DESCRIPTION

The specific embodiments of the present disclosure will be described in further detail below with reference to the drawings.

Figure 1:
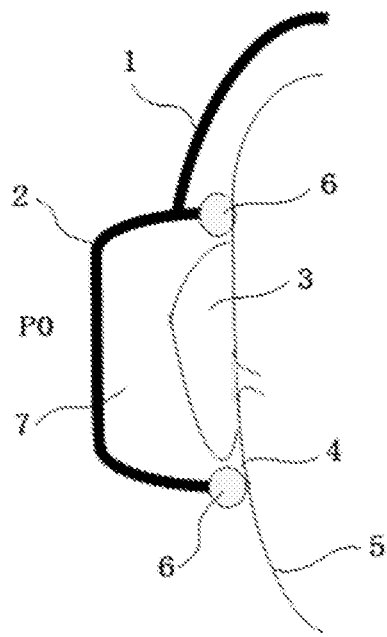
FIG. 1 is a partial structural diagram of a traditional earmuff.

Existing protective earmuffs for noise insulation generally include a headband 1, an earmuff shell 2, an ear-covering 6, etc., as shown in FIG. 1. In FIG. 1, there are two earmuff shells 2 connected together by the headband 1 which are configured to be worn respectively on the left ear and the right ear of the human body and play a protective role on the human ear. Each earmuff shell 2 forms an earmuff cavity 7, and an opening 4 is formed on one side of the earmuff shell 2 which faces the human ear, an outer pinna 3 of the wearer extends into the earmuff cavity 7 through the opening 4, thereby utilizing the earmuff shell 2 to block ambient noise and protect human hearing. In order to improve wearing comfort of the earmuff, an ear-covering 6 is often added at a position on the earmuff shell 2 where the opening 4 is formed. The ear-covering 6 is preferably made of highly compliant materials that are softer than muscles. By fitting the earmuff 6 to the facial muscle 5, discomfort to the wearer caused by direct contact of the skin and the hard earmuff shell 2 can be eliminated.

Figure 2:
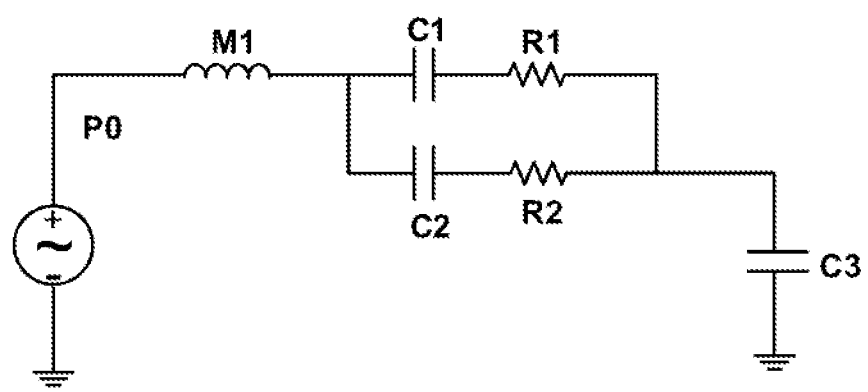
FIG. 2 is a schematic diagram of an equivalent circuit of a traditional earmuff being worn.

FIG. 2 is a schematic diagram of an equivalent circuit after wearing a protective earmuff shown in FIG. 1. In FIG. 2, M1 is the equivalent sound quality of the earmuff shell 2 and is equivalent to an electrical inductance; C1 is the equivalent acoustic compliance of the ear-covering 6 and is equivalent to an electrical capacitance; R1 is the equivalent acoustic resistance of the ear-covering 6 and is equivalent to an electrical resistance; C2 and R2 are respectively the equivalent acoustic compliance and acoustic resistance of facial muscle 5; C3 is the equivalent acoustic compliance of earmuff cavity 7. It can be seen from FIG. 2 that the sound quality M and the acoustic compliances C1, C2, and C3 form a low-pass filter circuit, and its corner frequency $f_0$ can be calculated from the following formula:

$$f_0 = \frac{1}{2\pi\sqrt{C \times L}};$$

wherein, C is the equivalent capacitance of the low-pass filter circuit, which is jointly determined by the equivalent acoustic compliance C1 of the ear-covering 6, the equivalent acoustic compliance C2 of the facial muscles 5 and the equivalent acoustic compliance C3 of the earmuff cavity 7, etc. After the equivalent acoustic compliances C1 and C2 are connected in parallel, they are then connected in series with the equivalent acoustic compliance C3 of the earmuff cavity 7. Considering that the equivalent acoustic compliance C2 of the facial muscle 5 is much smaller than the equivalent acoustic compliance C3 of the earmuff cavity 7, and plays a minor role in the equivalent capacitance C, therefore, the value of the equivalent capacitance C can be determined only by the equivalent acoustic compliances C1, C3 of the ear-covering 6 and the earmuff cavity 7. L is the equivalent inductance of the low-pass filter circuit, which can be determined from the equivalent sound quality M1 of the earmuff shell 2.

It is apparent from FIG. 2 that since the earmuff shell 1, the ear-covering 6 and the earmuff cavity 7 can form a low-pass filter (for a protective earmuff without the ear-covering 6, a low-pass filter can be formed by the earmuff shell 1 and the earmuff cavity 7), the protective earmuff can have a good high-frequency noise insulation effect. However, after the ambient noise P0 enters the earmuff cavity 7 through the earmuff shell 1, noise rise and amplification phenomenon would occur to passively insulated sound from the ambient noise near the corner frequency $f_0$ of the low-pass filter, as shown in the curve L1 in FIG. 5, thus generating greater low-frequency noise energy. For those who need to wear such protective earmuff for a long time, irreversible hearing damage will occur.

Figure 5:
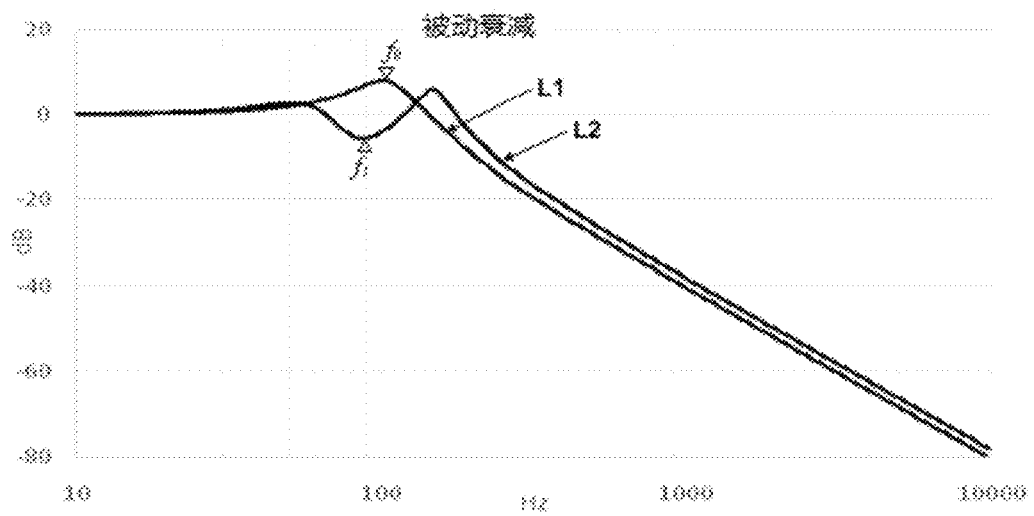
FIG. 5 is a comparison diagram of attenuation curves of passively insulated sound in an earmuff cavity.

It can be seen from the curve L1 in FIG. 5 that the noise entering the earmuff cavity 7 exhibits a second-order attenuation trend in the frequency band greater than the corner frequency $f_0$ (12 dB per octave), therefore, the lower the corner frequency $f_0$, the more effective the passive noise insulation of the protective earmuff.

In order to reduce the corner frequency $f_0$ and improve the noise insulation effect of the protective earmuff, the traditional design approach is to thicken the earmuff shell 2 and increase the earmuff cavity 7, thereby increasing the equivalent inductance L and equivalent capacitance C of the low-pass filter circuit to reduce the corner frequency $f_0$. However, this traditional design approach will cause the protective earmuff to become large and bulky and inconvenient to wear.

In order to solve the above problem, in this embodiment, a low-frequency resonator is provided in the earmuff cavity 7, and the resonance sound absorption effect of the low-frequency resonator is used to absorb noise energy near the resonance frequency in the earmuff cavity 7, thus achieving a design purpose of reducing the noise in the earmuff cavity 7.

The following describes in detail the specific structural design of the noise-reducing earmuff provided with a low-frequency resonator through two specific embodiments.

Embodiment 1

Figure 3:
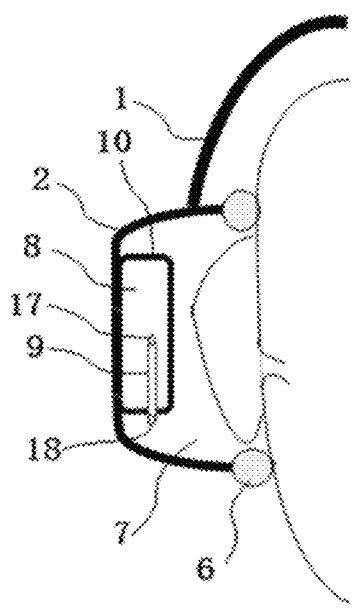
FIG. 3 is a partial structural diagram of an embodiment of a noise-reducing earmuff proposed by the present disclosure.

As shown in FIG. 3, in this embodiment, in order to form a low-frequency resonator in an earmuff, a separator 10 is added in an earmuff cavity 7 enclosed by an earmuff shell 2, and the separator 10 is used to form an independent chamber 8 in the earmuff cavity 7, and a conduit 9 is installed on the separator 10. The conduit 9 is hollow with openings at two ends, with one end with the opening 17 extends into the chamber 8 and the other end with the opening 18 extends out of the chamber 8 and is located in the earmuff cavity 7.

Figure 4:
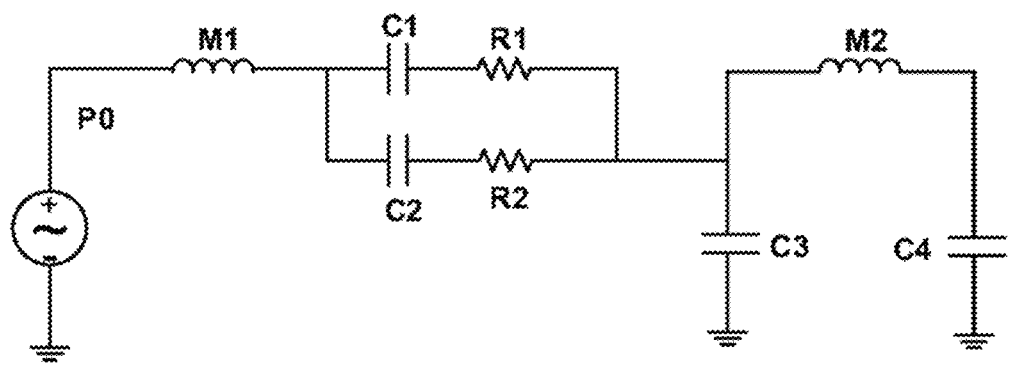
FIG. 4 is a schematic diagram of an equivalent circuit of the noise-reducing earmuff shown in FIG. 3 being worn.

FIG. 4 is a schematic diagram of an equivalent circuit after wearing the noise-reducing earmuff provided with a low-frequency resonator. In FIG. 4, M1 is the equivalent sound quality of the earmuff shell 2; C1 and R1 are the equivalent acoustic compliance and acoustic resistance of the ear-covering 6 respectively; C2 and R2 are respectively the equivalent acoustic compliance and acoustic resistance of the facial muscle 5; C3 is the equivalent acoustic compliance of the earmuff cavity 7; M2 is the equivalent sound quality of the conduit 9 and is equivalent to the electrical inductance; C4 is the equivalent acoustic compliance of the chamber 8 and is equivalent to the electrical capacitance. It can be seen from FIG. 4 that the sound quality M2 and the acoustic compliance C4 can form a low-frequency resonator, and its resonance frequency $f_1$ can be calculated from the following formula:

$$f_1 = \frac{1}{2\pi\sqrt{C' \times L'}};$$

Wherein C' is the equivalent capacitance of the low-frequency resonator, which is determined by the equivalent acoustic compliance C4 of the chamber 8. L' is the equivalent inductance of the low-frequency resonator, which can be determined by the equivalent sound quality M2 of the conduit 9.

Since the low-frequency resonator has a resonance sound absorption effect that absorbs sound energy near its resonance frequency $f_1$, the resonance frequency $f_1$ of the low-frequency resonator can be changed by adjusting the spatial volume of the chamber 8 and/or the shape of the conduit 9. By adjusting the resonance frequency $f_1$ of the low-frequency resonator to be equivalent (i.e., same or close) to the corner frequency $f_0$ of the low-pass filter formed by the earmuff, the resonance sound absorption effect of the low-frequency resonator near its resonance frequency $f_1$ can be used to absorb the noise energy of passively insulated sound near the corner frequency $f_0$ of the low-pass filter, thus solving the problem of noise rise and noise amplification of the passively insulated sound in the earmuff cavity 7 generated near the corner frequency $f_0$ and effectively attenuating the low-frequency noise in the earmuff cavity 7 and then achieving the purpose of noise-reducing.

The curve L2 in FIG. 5 is the noise attenuation curve after the low-frequency resonator is provided in the earmuff. It can be seen from the curve L2 that the noise is substantially absorbed near the resonance frequency $f_1$ of the low-frequency resonator. Although in the frequency band greater than the resonance frequency $f_1$, the noise is slightly higher than that without the addition of a low-frequency resonator, the amplitude of the increase and the width of the frequency band are very small, and the amount of noise insulation in the high-frequency part has reached dozens of dB, therefore, the impact of the noise increasing problem on the wearer is negligible, and the effective protection for the wearer's hearing is achieved.

In this embodiment, the chamber 8 can be filled with sound absorbing materials such as sound absorbing sponge or glass wool felt to expand the chamber space of the low frequency resonator, that is, to increase the equivalent acoustic compliance C4 of the chamber 8, thus reducing the resonance frequency $f_1$ of the low-frequency resonator. The conduit 9 can be selected from various air pipes that can produce sound quality, such as hosepipe and hard-pipe, its form can be straight pipe, bent pipe and its cross-sectional shape can be round, square or other shapes. As a preferred design of this embodiment, the equivalent acoustic compliance C4 of the chamber 8 may be set to 20 cc (cubic centimeter), and the conduit 9 can use a round pipe with a diameter of 1.5 mm and a length of 10 mm.

Figure 6:
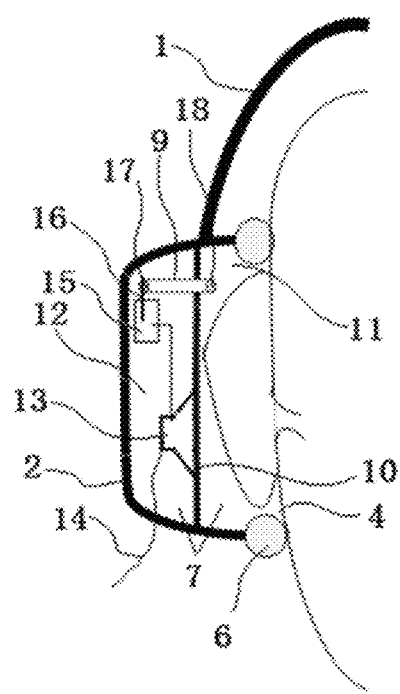
FIG. 6 is a partial structural diagram of an embodiment in which a low-frequency resonator is provided in a headphone.

Applying the design principle of the low-frequency resonator of this embodiment to the current headphone can make the headphone have the function of noise reduction and protection. Specifically, as shown in FIG. 6, the current headphone generally includes a headband 1 and two earmuff shells 2 (left and right), each earmuff shell 2 surrounds an earmuff cavity 7 with an opening 4 formed on one side, a separator 10 is provided in each earmuff cavity 7, the separator 10 is preferably provided parallel to the opening 4, and the earmuff cavity 7 is divided into two parts by the separator 10, wherein one cavity with the opening 4 can be referred to as the front cavity 11 of the earphone, and the other cavity can be referred to as the rear cavity 12 of the speaker, which is used to accommodate the sound-generating device of the earphone—the speaker 13 (or loudspeaker). The speaker 13 is connected to the host through the earphone lead 14 and receives the audio signal from the host. In this embodiment, the conduit 9 is provided on the separator 10, an opening 17 at one end of the conduit 9 is located in the rear cavity 12 of the speaker, and the opening 18 at the other end is located in the front cavity 11 of the earphone, and the rear cavity 12 of the speaker is used to form a low-frequency resonator with the conduit 9, thus absorbing the low-frequency noise near the resonance frequency in the earphone. The spatial volume of the rear cavity 12 of the speaker and shape design of the conduit 9 can be modeled on the relevant description of FIG. 3 above.

Considering that when the earphone is working normally, most of the audio signals output through the speaker 13 are low-frequency signals, and inevitably include audio signals near the resonance frequency. If the low-frequency resonator formed by the rear cavity 12 of the speaker and the conduit 9 are allowed to function during the normal operation of the earphone, the audio signal near the resonance frequency will be absorbed, with the result that the sound unable to output normally. In order to solve this problem, this embodiment adds a separator 16 in the rear cavity 12 of the speaker, as shown in FIG. 6. The separator 16 is designed to block the opening 17 of the conduit 9 located in the rear cavity 12 of the speaker when the speaker 13 outputs sound, so as to destroy the low frequency resonator, thereby preventing the low frequency energy in the audio signal or communication signal from being cancelled. When the speaker 13 has no sound output, the separator 16 can be designed to be apart from the opening 17 of the conduit 9 in the rear cavity 12 of the speaker, and then the low-frequency resonator formed by the rear cavity 12 of the speaker and the conduit 9 can be used to absorb the low-frequency noise energy in the earmuff cavity 7 to achieve the noise reduction and protection function of the earphone.

As a preferred structural design of this embodiment, an armature in the electromagnetic relay 15 (the armature is used in the electromagnetic relay to drive the movable contact to pull in or disconnect) can be used as the separator 16 for blocking the opening 17 of the conduit 9. Specifically, the electromagnetic relay 15 can be designed to be energized when the speaker 13 receives an audio signal, so that its coil generates a magnetic field, attracting the armature to displace (for example, approaching in the direction of the coil), thus blocking the opening 17 of the conduit 9 located in the rear cavity 12 of the speaker. Conversely, when the speaker 13 receives no audio signal, the electromagnetic relay 15 is designed to be de-energized, and at the moment its coil no longer generates a magnetic field, releasing the armature (for example, the armature moves apart from the coil) to keep the armature apart from the opening 17 of the conduit 9 in the rear cavity 12 of the speaker. At this time, the opening 17 of the conduit 9 is exposed to the rear cavity 12 of the speaker, and forms a low-frequency resonator with the rear cavity 12 of the speaker, so as to absorb the low-frequency noise in the earmuff cavity 7 to achieve the noise reduction effect.

Figure 7:
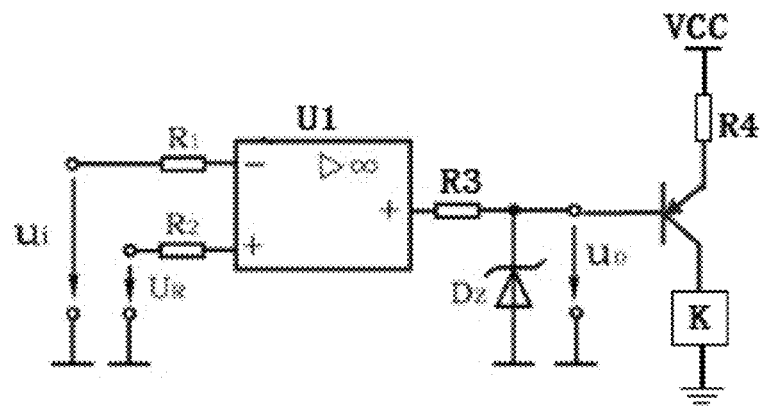
FIG. 7 is a circuit schematic diagram of an embodiment of an control section of the electromagnetic relay in FIG. 6.

In order to control the armature in the electromagnetic relay 15 to act accurately, in this embodiment, a relay control circuit is further provided in the rear cavity 12 of the speaker, as shown in FIG. 7, specifically provided on the PCB-board of the earphone, so as to realize the accurate control of the electromagnetic relay. Specifically, a comparator U1 is provided in the relay control circuit, an inverting input terminal of the comparator U1 is connected to the speaker 13 through a resistor R1, and the audio signal Ui transmitted to the speaker 13 is received. The non-inverting input terminal of the comparator U1 is connected to a trigger voltage UR through a resistor R2, and the output terminal of the comparator U1 is connected to a control terminal of a switching element through a resistor R3, for example, to a base electrode of a PNP-type triode Q1, and a switching path of the switching element is connected in the power supply circuit of the coil K of the electromagnetic relay, for example, a collector electrode of the PNP-type triode Q1 is grounded through the coil K of the electromagnetic relay connected in series therewith, and an emitting electrode is connected to a DC power supply VCC through a current limiting resistor R4.

Set the amplitude of the trigger voltage UR to be smaller than the amplitude of the bias voltage in the audio signal Ui, and when the speaker 13 does not receive the audio signal Ui, the voltage at the non-inverting input terminal of the comparator U1 is higher than the voltage at its inverting input terminal, and at this moment the comparator U1 outputs a high level, that is, Uo in FIG. 7 is the high level, and is equivalent to the amplitude of the DC power supply VCC. At this time, the PNP-type triode Q1 is in the cut-off state, no current passes through the coil K of the electromagnetic relay and no magnetic field is generated around the coil K, the armature in the electromagnetic relay is kept apart from the default position of the coil K, the armature is designed to be apart from the opening 17 of the conduit 9 at the default position, so that the conduit 9 and the rear cavity 12 of the speaker form a low-frequency resonator for eliminating low-frequency noise in the earmuff cavity 7. At this time, the earphone can be used as a noise protection earmuff to insulate ambient noise. When the speaker 13 receives the audio signal Ui, since the bias voltage in the audio signal Ui is higher than the trigger voltage UR, the voltage Uo output through the comparator U is low level. At this time, the PNP-type triode Q1 is saturated and conducted, the DC power supply VCC is used to supply the coil K in the electromagnetic relay to generate a magnetic field around the coil K, attracting the armature to move closer to the coil K, thereby blocking the opening 17 of the conduit 9, so that the conduit 9 and the rear cavity 12 of the speaker cannot form a low-frequency resonator, thus preventing the low-frequency energy in the audio signal or the communication signal from being cancelled, and ensuring that the audio signal is output normally through the speaker 13 and the communication signal can be reliably transmitted.

Of course, the comparator U1 can also receive the trigger voltage UR through its inverting input terminal and receive the audio signal Ui through its non-inverting input terminal. At this time, the switching element Q1 can be an NPN-type triode connected in the power supply circuit of the coil K of the electromagnetic relay. In the same way, it is also possible to achieve accurate control of the power on and off of the coil K.

In this embodiment, the resistors R1, R2, R3 are protection resistors, used to protect the comparator U1 from being damaged by the impact of abnormal current, and by adjusting the resistance values of the protection resistors R1, R2, R3, the sensitivity of the comparator U1 is reduced to ensure that the alternately changing voice signal can control the triggering of the comparator U1 stably.

At the output terminal of the comparator U1, a voltage stabilizing diode Dz can be further connected. When the voltage of the audio signal Ui is less than the trigger voltage UR, the voltage stabilizing diode Dz is used to clamp the voltage Uo output from the comparator U1 at the high level of the voltage stabilizing diode Dz corresponding to the reverse drop voltage, and the switching element Q1 is controlled to maintain the off state, thus keeping the armature apart from the opening 17 of the conduit 9, and the low-frequency resonator formed by the conduit 9 and the rear cavity 12 of the speaker is used to absorb more low-frequency noise energy in the earphone.

Embodiment 2

Figure 8:
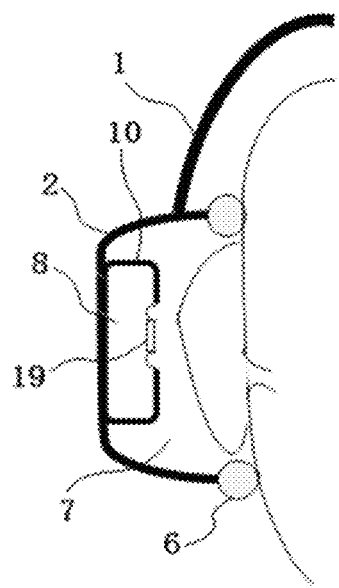
FIG. 8 is a partial structural diagram of another embodiment of a noise-reducing earmuff proposed by the present disclosure.

As shown in FIG. 8, in this embodiment, in order to form a low-frequency resonator in the earmuff, first, a separator 10 is provided in the earmuff cavity 7 formed by the earmuff shell 2, and the separator 10 is used to form an independent chamber 8 in the earmuff cavity 7. Then, a passive radiator 19 is installed on the separator 10, and the passive radiator 19 and the cavity 8 form a low-frequency resonator to absorb low-frequency noise near the resonance frequency in the earmuff cavity 7. With this structural design, when calculating the resonance frequency $f_1$ of the low-frequency resonator, the equivalent capacitance C' of the low-frequency resonator is determined by the equivalent acoustic compliance of the chamber 8, and the equivalent inductance L' of the low-frequency resonator is determined by the equivalent sound quality of the passive radiator 19. Since the equivalent sound quality of the passive radiator 19 is generally greater than the equivalent sound quality of the conduit 9, the low-frequency resonator formed by the passive radiator 19 and the chamber 8 can obtain a lower resonance frequency, which is beneficial to absorbing lower frequency noise.

Figure 9:
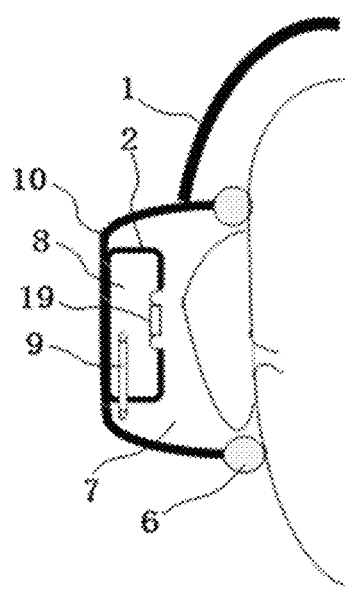
FIG. 9 is a partial structural diagram of yet another embodiment of a noise-reducing earmuff proposed by the present disclosure.

Of course, on the basis of the earmuff structure design shown in FIG. 8, a conduit 9 may be further added to the separator 10, as shown in FIG. 9, and one of the two openings at two ends of the conduit 9 extends into the chamber 8, and the other extends out from the chamber 8 and is located in the earmuff cavity 7, the passive radiator 19, the conduit 9 and the chamber 8 are used to form a low-frequency resonator to cancel low-frequency noise at lower frequencies and wider bandwidths.

When the low-frequency resonator is composed of a passive radiator 19, a conduit 9 and a chamber 8, the equivalent inductance L' in the calculation formula of the resonance frequency $f_1$ of the low-frequency resonator should be determined jointly by the equivalent sound quality of the passive radiator 19 and the conduit 9, and the equivalent capacitance C' of the low-frequency resonator is determined by the equivalent acoustic compliance of the chamber 8.

The spatial volume of the chamber 8 or the shape of the passive radiator 19 and the conduit 9 is adjusted so that the resonance frequency $f_1$ of the low-frequency resonator is equal to or close to the corner frequency $f_0$ of the low-pass filter formed by the earmuff (for the earmuff provided with the ear-covering 6, $f_0$ is determined by the equivalent inductance of the earmuff shell 2 and the equivalent capacitance of the earmuff cavity 7 and the ear-covering 6) to absorb noise energy near the resonance frequency $f_1$ and to prevent the noise in the earmuff cavity 7 from being raised and amplified near the resonance frequency $f_1$.

Considering the limited space of the earmuff cavity 7, in this embodiment, it is preferable to fill the cavity 8 with a sound absorbing material such as sound absorbing sponge or glass wool felt to expand the space of the cavity 8.

According to the foregoing embodiment 2, the aspect 1 of the present disclosure provides a noise-reducing earmuff, including:

an earmuff shell, which forms an earmuff cavity;

a separator, which is installed in the earmuff cavity and forms an independent cavity;

a passive radiator, which is installed on the separator, wherein the chamber and the passive radiator form a low-frequency resonator whose resonance frequency is equivalent to the corner frequency of a low-pass filter formed by the earmuff.

According to the above aspect 1, the aspect 2 of the present disclosure provides a noise-reducing earmuff, wherein an opening is formed on one side of the earmuff shell which faces the human ear, and an ear-covering is installed on the earmuff shell at the opening, and the corner frequency of the low-pass filter is determined by the equivalent inductance of the earmuff shell and the equivalent capacitance of the earmuff cavity and ear-covering.

Further, according to the foregoing embodiment 2, the aspect 3 of the present disclosure provides a noise-reducing earmuff, including:

an earmuff shell, which forms an earmuff cavity;

a separator, which is installed in the earmuff cavity and forms an independent cavity;

a passive radiator, which is installed on the separator;

a conduit, which is installed on the separator, the conduit being provided with an opening at each of two ends thereof, wherein one of the openings being located in the chamber, and the other extending out of the chamber and being located in the earmuff cavity; the cavity, the passive radiator and the conduit form a low-frequency resonator whose resonance frequency is equivalent to the corner frequency of the low-pass filter formed by the earmuff.

According to the above aspect 3, the aspect 4 of the present disclosure provides a noise-reducing earmuff, wherein an opening is formed on one side of the earmuff shell which faces the human ear, and an ear-covering is installed on the earmuff shell at the opening, and the corner frequency of the low-pass filter is determined by the equivalent inductance of the earmuff shell and the equivalent capacitance of the earmuff cavity and ear-covering.

Of course, the above description is not a limitation of the present disclosure, and the present disclosure is not limited to the above examples. Changes, modifications, additions or replacements made by those of ordinary skill in the art within the substantive scope of the present disclosure should also belong to the scope of protection of this disclosure.

The invention claimed is:

1. A noise-reducing earmuff, comprising: an earmuff shell, forming an earmuff cavity; a separator, being installed in the earmuff cavity and forming an independent chamber; and a conduit being installed on the separator, the conduit being provided with an opening at each of two ends thereof; wherein one of the openings being located in the chamber, and the other extending out of the chamber and being located in the earmuff cavity; wherein the chamber and the conduit form a low-frequency resonator whose resonance frequency is equivalent to a corner frequency of a low-pass filter formed by the earmuff, wherein the earmuff is in a headphone, the chamber is a rear cavity of a speaker in the earmuff, and a separator is provided in the rear cavity of the speaker, wherein the separator is configured such that when the speaker outputs sound, the separator blocks the opening of the conduit located in the chamber; and when the speaker outputs no sound, the separator is apart from the opening of the conduit located in the chamber.

2. The noise-reducing earmuff according to claim 1, characterized in that an opening is formed on one side of the earmuff shell which side faces a human ear, and an ear-covering is installed on the earmuff shell at the opening, wherein the corner frequency of the low-pass filter is determined by an equivalent inductance of the earmuff shell and an equivalent capacitance of the earmuff cavity and the ear-covering.

3. The noise-reducing earmuff according to claim 1, characterized in that the chamber is filled with a sound absorbing material.

4. The noise-reducing earmuff according to claim 1, characterized in that, the separator is an armature in an electromagnetic relay, wherein when the speaker receives an audio signal, the electromagnetic relay generates a magnetic field to displace the armature by attraction and block the opening of the conduit located in the chamber; when the speaker receives no audio signal, the electromagnetic relay releases the armature to keep the armature apart from the opening of the conduit located in the chamber.

5. The noise-reducing earmuff according to claim 4, characterized by also comprising a comparator, wherein the comparator has two input terminals configured to respectively receive a trigger voltage and the audio signal, wherein the output terminal is connected to a control terminal of a switching element, and a switching path of the switching element is connected in a power supply circuit of a coil of the electromagnetic relay; and the amplitude of the trigger voltage is lower than the amplitude of a bias voltage in the audio signal, wherein when an audio signal is received, an output level of the comparator controls the switching element to conduct, and the power supply circuit of the coil of the electromagnetic relay is connected, and a magnetic field is generated by the coil to displace the armature by attraction, thus blocking the opening of the conduit located in the chamber.

* * * * *